United States Patent
Brunner et al.

(10) Patent No.: US 7,689,042 B2
(45) Date of Patent: Mar. 30, 2010

(54) METHOD FOR CONTOUR VISUALIZATION OF REGIONS OF INTEREST IN 2D FLUOROSCOPY IMAGES

(75) Inventors: Thomas Brunner, Nürnberg (DE); Frank Deinzer, Röthenbach (DE)

(73) Assignee: Siemens Aktiengesellschaft, Munich (DE)

( * ) Notice: Subject to any disclaimer, the term of this patent is extended or adjusted under 35 U.S.C. 154(b) by 943 days.

(21) Appl. No.: 11/479,182

(22) Filed: Jun. 30, 2006

(65) Prior Publication Data
US 2007/0003016 A1 Jan. 4, 2007

(30) Foreign Application Priority Data
Jun. 30, 2005 (DE) .................. 10 2005 030 646

(51) Int. Cl.
*G06K 9/48* (2006.01)

(52) U.S. Cl. .................. 382/199; 378/4; 378/42; 378/62; 382/128; 382/154; 600/410; 600/424; 600/426

(58) Field of Classification Search .......... 378/4, 378/8, 62, 98.12, 42; 382/128, 154, 199; 600/409, 410, 426
See application file for complete search history.

(56) References Cited

U.S. PATENT DOCUMENTS

| | | | |
|---|---|---|---|
| 6,856,827 B2 * | 2/2005 | Seeley et al. | 600/426 |
| 7,010,080 B2 | 3/2006 | Mitschke et al. | |
| 7,117,027 B2 * | 10/2006 | Zheng et al. | 600/426 |
| 7,327,872 B2 * | 2/2008 | Vaillant et al. | 382/154 |
| 7,344,307 B2 * | 3/2008 | Yatsenko et al. | 378/207 |
| 7,542,791 B2 * | 6/2009 | Mire et al. | 600/407 |
| 2003/0181809 A1 | 9/2003 | Hall et al. | |
| 2003/0220555 A1 * | 11/2003 | Heigl et al. | 600/407 |
| 2004/0101086 A1 | 5/2004 | Sabol et al. | |
| 2004/0215071 A1 * | 10/2004 | Frank et al. | 600/407 |
| 2005/0085714 A1 * | 4/2005 | Foley et al. | 600/424 |
| 2005/0135558 A1 * | 6/2005 | Claus et al. | 378/42 |
| 2006/0013459 A1 | 1/2006 | Katscher et al. | |
| 2006/0023840 A1 * | 2/2006 | Boese | 378/98.12 |
| 2006/0061570 A1 * | 3/2006 | Cheryauka et al. | 345/424 |
| 2006/0182326 A1 * | 8/2006 | Schildkraut et al. | 382/132 |
| 2007/0003016 A1 * | 1/2007 | Brunner et al. | 378/98.12 |
| 2009/0105579 A1 * | 4/2009 | Garibaldi | 600/409 |

FOREIGN PATENT DOCUMENTS

| | | |
|---|---|---|
| DE | 102 10 646 A1 | 10/2003 |
| DE | 102 14 254 A1 | 10/2003 |
| DE | 103 56 011 A1 | 6/2004 |
| DE | 103 22 738 A1 | 12/2004 |
| WO | WO 03/059166 A2 | 7/2003 |
| WO | WO 2005/024721 A2 | 3/2005 |

* cited by examiner

*Primary Examiner*—Gregory M Desire

(57) ABSTRACT

The invention relates to a method, which assists the doctor in orientation in 2D fluoroscopy images. The invention relates to a method for contour visualization of regions of interest in fluoroscopy images by: firstly generating a 3D raw data set comprising at least one region of interest in which the contour of the at least one region of interest is visible, secondly generating a segmented 3D data set from the 3D raw data set in which the contour in at least one region of interest is clearly delimited, thirdly generating a 2D fluoroscopy image which contains the at least one region of interest, fourthly generating a 2D projection from the segmented 3D data set which is congruent with the 2D fluoroscopy image, fifthly determining the optionally approximated contour of the at least one region of interest in the 2D projection, and finally overlaying the contour with the 2D fluoroscopy image.

16 Claims, 3 Drawing Sheets

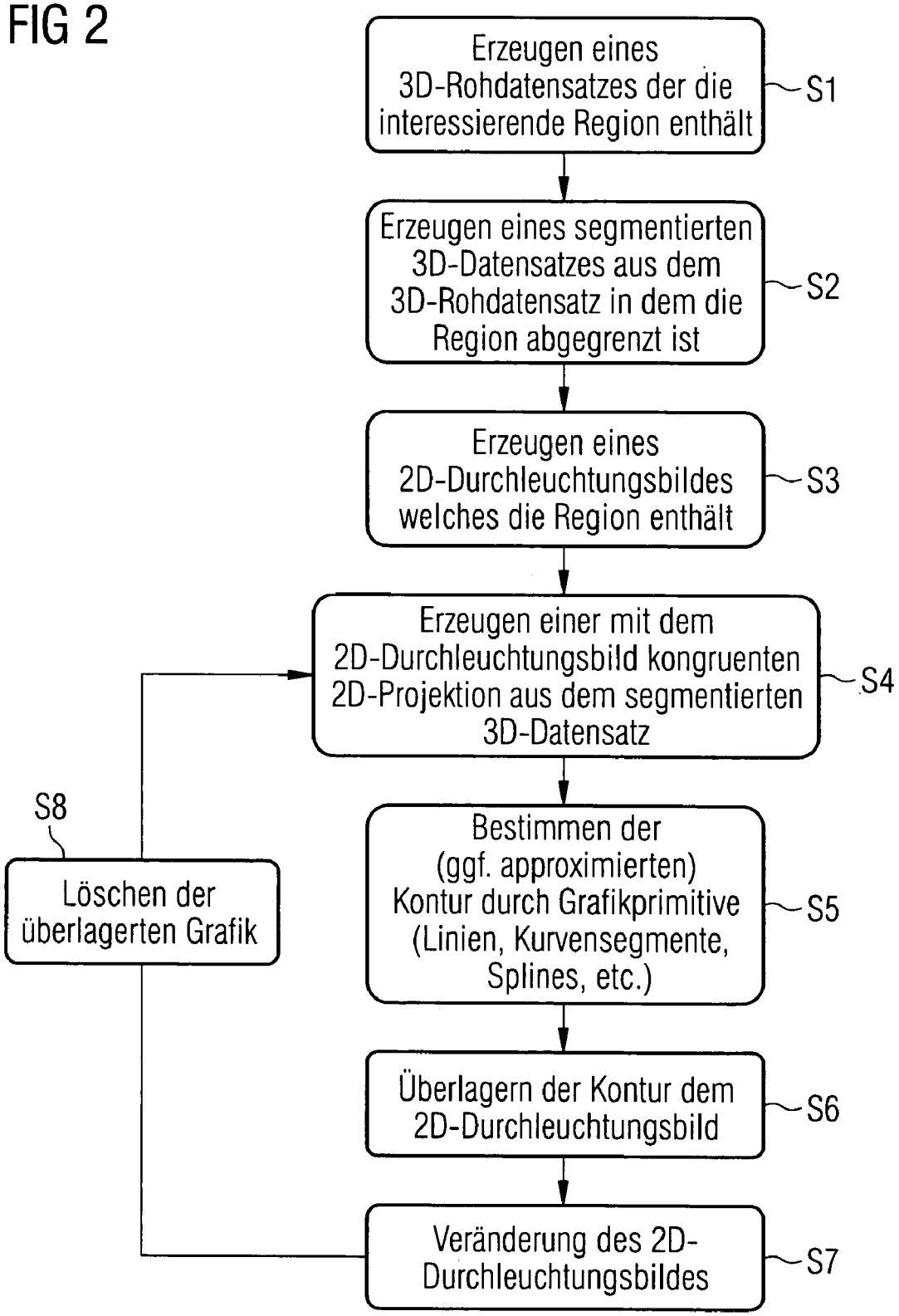

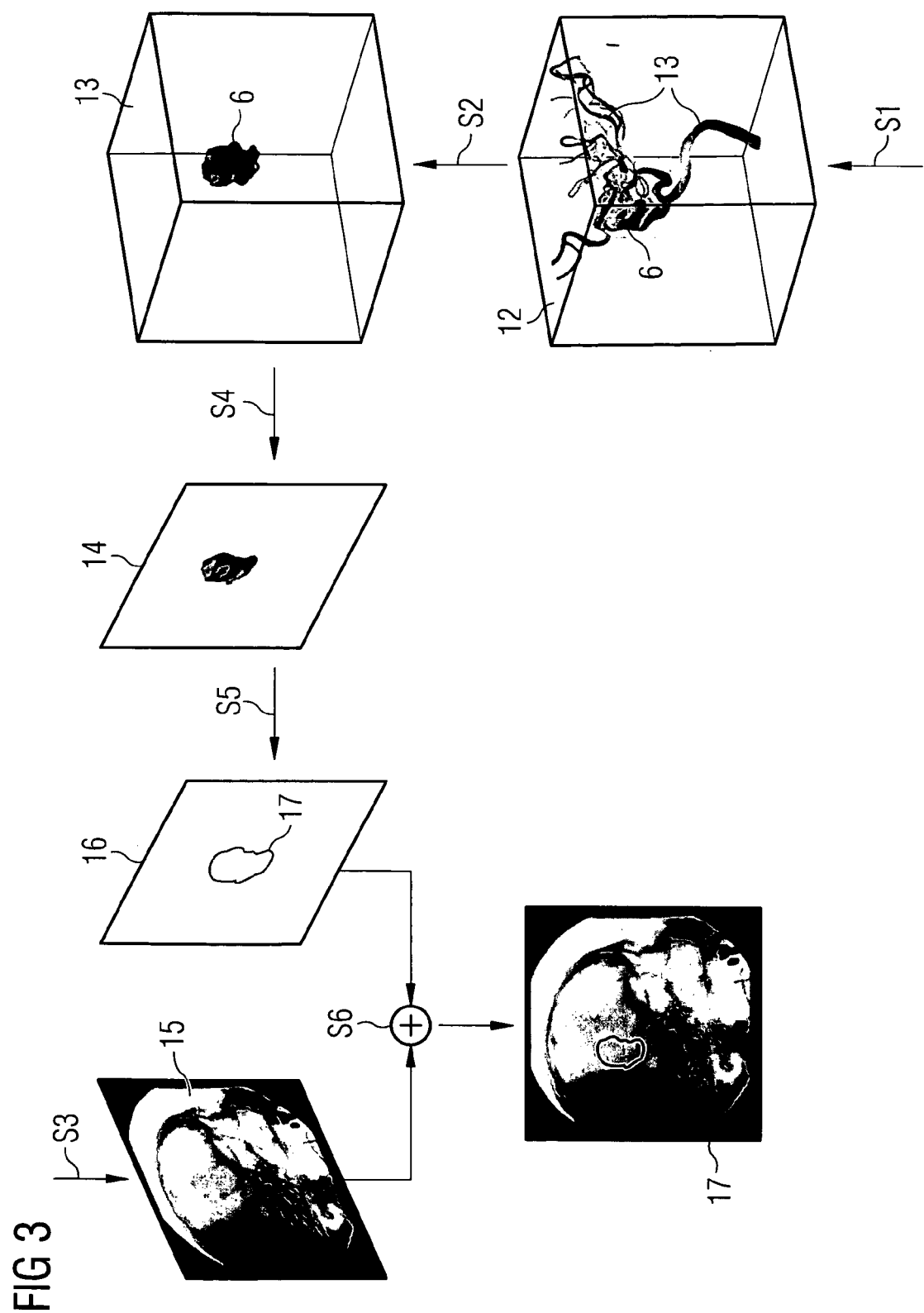

METHOD FOR CONTOUR VISUALIZATION OF REGIONS OF INTEREST IN 2D FLUOROSCOPY IMAGES

CROSS REFERENCE TO RELATED APPLICATIONS

This application claims priority of German application No. 10 2005 030 646.2 filed Jun. 30, 2005, which is incorporated by reference herein in its entirety.

FIELD OF THE INVENTION

The present invention relates to a method, which assists a doctor in orientation in 2D fluoroscopy images for instance. The present invention relates here to a method which provides a graphically clear and distinct orientation aid during interventions under x-ray control.

BACKGROUND OF THE INVENTION

Examinations or treatments of an (ill) patient are increasingly carried out in a minimally invasive manner, i.e. with as little operative effort as possible. Examples of such procedures are treatments using endoscopes, laparoscopes, catheters or biopsy needles, which are inserted into the examination area of the patient, subsequently referred to as "region of interest" or "area of interest", via a small opening in the body in each instance. By way of example, catheters are frequently used within the scope of angiographic or cardiological examinations.

The initial problem from a medical-technology perspective lies in clearly identifying a region of interest (e.g. a tumor), i.e. in recognizing its contours, in a 2D fluoroscopy image, recorded for instance using a conventional x-ray device or using an x-ray C-arm. The present invention concerns the solution to this problem.

The problem described is particularly prominent if the region of interest within the scope of an operation or examination must be approached using a medical instrument. This could conceivably be—without restricting general applicability—a biopsy needle or a catheter which can be visualized precisely and with a high resolution in one or more 2D fluoroscopy images by means of an intraoperative x-ray control, e.g. with the so-called C-arm, but however the representation of the anatomy of the patient, in particular the representation of the pathogenous regions of interest (tumor, aneurism, stenosis etc.) would be inadequate and unsuitable with these types of control recordings to provide the doctor with an orientation aid. Precise localization of the affected area in the body is thus very difficult.

Numerous approaches exist in the prior art to assist the doctor in orientation within the body using intraoperative x-ray control.

The oldest and thus also the best-known method consists in injecting contrast medium, taking an instantaneous x-ray, storing this as a reference image and underlaying a current (intraoperative) fluoroscopy. It is however again disadvantageous that this process must be repeated with each new angulation of the C-arm or other changes in the (angiography) system (e.g. changes by means of zoom, SID—Source Image Distance, table displacement etc.).

A further method consists of first acquiring a volume data set of the relevant body area, which fully includes the region of interest and/or the diseased organ or tissue or organ or tissue to be diagnosed. This is carried out for instance by (contrast medium-based) spiral computer tomography or other 3D imaging modalities. (In MRT recordings, tumors are also visible without contrast medium for instance.) Furthermore, an artificial 3D volume projection image is generated on the basis of the 3D data set, which is to be viewed from the same perspective as the current fluoroscopy image and is also underlaid on this image. Reference is also made in this context to "artificial projection" of the 3D volume.

External (infrared-based, magnetic etc.) navigation systems also exist, which determine the 3D position of a medical instrument (catheter, needle) by means of external position sensors and allow an orientation within a previously recorded volume data set on the basis of this information.

The common factor in all 3D-based methods is a photorealistic underlay of a (3D) reference image relating to a current (intraoperative) fluoroscopy image with the disadvantage of a largely inconcise representation of the anatomy, which unsettles the doctor rather than aids him/her.

SUMMARY OF THE INVENTION

The object of the present invention is to provide a clear, simple and thus concise orientation aid in fluoroscopy images, for instance with minimally-invasive operations using x-ray control, said orientation aid facilitating the navigation.

This object is achieved in accordance with the present invention by the features of the independent claims. The dependent claims form the central concept of the invention in a particularly advantageous manner.

A method is claimed for contour visualization of regions of interest in fluoroscopy images, comprising the following steps:

S1: Generating a 3D raw data set comprising at least one region of interest, in which 3D raw data set the contour of the at least one region of interest is visible, S2: Generating a segmented 3D data set from the 3D raw data set in which the contour is clearly delimited in at least one region of interest.

S3: Generating a 2D fluoroscopy image which contains the at least one region of interest, S4: Generating a 2D projection from the segmented 3D data set, which is congruent with the 2D fluoroscopy image, S5: Determining the optionally approximated contour of the at least one region of interest in the 2D projection, and S6: Overlaying the contour with the 2D fluoroscopy image.

In a particularly advantageous embodiment of the method according to the invention, the 2D fluoroscopy image is intraoperatively obtained, possibly monitored for an intraoperative change and steps S4 to S6 repeated in the event of an intraoperative change in the 2D fluoroscopy image.

In accordance with the invention the 3D raw data set determined at the start can be obtained preoperatively with any imaging modality.

The region of interest is advantageously clearly delimited by means of automatic or manual segmentation.

The 2D projection is advantageously generated by a 2D-3D registration, with this 2D-3D registration being carried out in an image-based or marker-based manner.

The contour is determined in accordance with the invention by means of manual or automatic segmentation and is furthermore optionally advantageously approximated by graphic primitives such as lines, curves, splines etc.

A device is further claimed, which is suited to implementing a method according to one of the preceding claims.

BRIEF DESCRIPTION OF THE DRAWINGS

Further advantages, features and characteristics of the present invention are now described in more detail with reference to exemplary embodiments relating to the attached drawings, in which;

FIG. 2 shows a flow diagram of the method according to the invention and

FIG. 3 shows the image processing steps on the image data sets in question according to the invention.

DETAILED DESCRIPTION OF THE INVENTION

Figure 1:
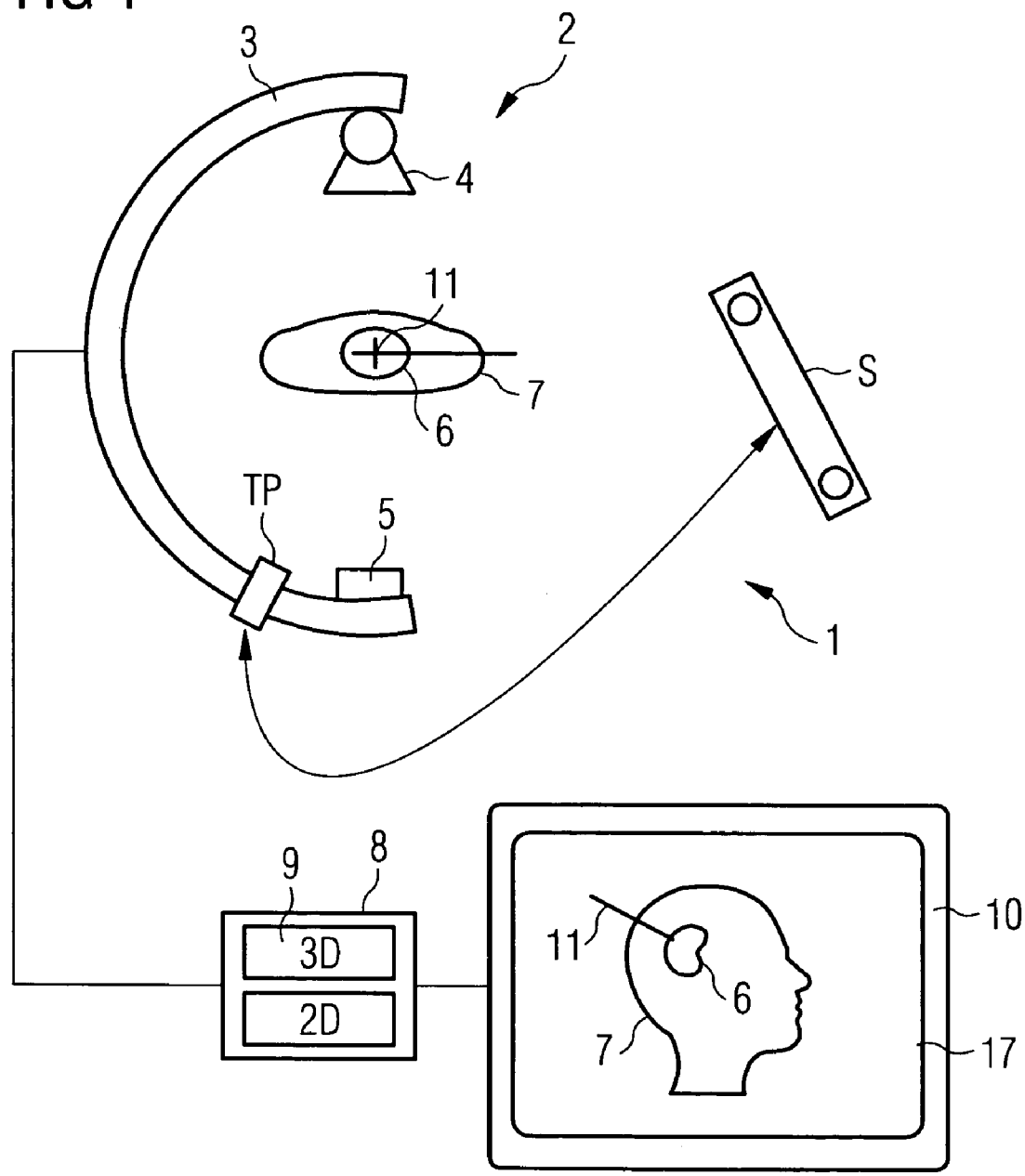
FIG. 1 shows a schematic representation of a main drawing of an examination and/or treatment device possible for the method according to the invention.

The method according to the invention can be applied to any existing 2D fluoroscopy images, independent of a medical intervention, but is however explained below with reference to an intraoperative minimally-invasive measure under x-ray control, since the latter represents the most important application of the method according to the invention.

FIG. 1 shows a basic diagram of a possible examination and/or treatment device 1 used within the scope of the method according to the invention for minimally invasive operations under x-ray control. The device 1 comprises a C-arm 3 for recording two-dimensional fluoroscopy images (2D fluoroscopy images and/or 2D fluoro images), on which an x-ray source 4 and a radiation detector 5, e.g. a fixed body image detector and a tool plate TP, are arranged. The examination area 6 of a patient 7 is preferably located in the isocenter of the C-arm, so that it can be viewed in full in the recorded fluoroscopy images.

A navigation sensor S is located in the immediate vicinity to the C-arm, by means of which navigation sensor S the current position of the tool plate TP, and thus that of the C-arm as well as the position of a medical instrument 11 used for the operation and of the patient can be detected.

The operation of the device 1 is controlled via a control and processing device 8, which also controls inter alia the image recording operation.

It further comprises an image processing device (not shown in further detail) with one or a number of monitors 10, on which (a) fluoroscopy image(s) is/are displayed.

A 3D raw data set 9 exists inter alia in the image processing device, which 3D raw data set 9 was preferably recorded preoperatively and in particular contains the region of interest (pathological area) in full such that this appears to be delimited and/or can be delimited compared with the surrounding tissue. This 3D raw data set 9 could have been recorded using any imaging modality, provided this ensures a clear delimitation.

In the case of a computer tomography recording, this should be carried out in a contrast medium-based manner in order to display soft tissue (tumor).

MRT recordings generally do not require any specific recording conditions, although in many cases, these contrast medium-based recordings result in improved images. The 3D raw data set 9 could have also been recorded using the own image recording device 2, in other words, immediately before the actual intervention, with the image recording device 2 then needing to be operated in 3D angiography mode.

The present invention now provides a method, with which the examination area (6) (in other words the region of interest) overlays a current 2D fluoroscopy image recorded intraoperatively in any C-arm position in a clear and notedly concise manner, said fluoroscopy image essentially only clearly imaging the medical instrument.

It has been shown that the treating doctor is, in most cases, not interested in a realistic overlay and wants an orientation aid which only indicates the borders or contours of a tumor for instance.

To realize this, the following procedure is proposed in accordance with the invention (see method flow diagram of FIG. 2 in conjunction with FIG. 3):

The method is based on a (preoperative) 3D raw data set 9, said 3D raw data set containing the region of interest 6 embedded in the surrounding tissue 13. In FIG. 3, such a surrounding tissue 13 exhibits an angiographic structure.

In a first method step S1, the 3D raw data set 9 is acquired in such a way that the region 6 of interest (the tumor for instance) can be clearly delimited from surrounding tissue 13. In a second method step S2, such a delimitation is carried out by means of manual or automatic segmentation, whereby a segmented 3D data set 12 is obtained, which still only contains the region of interest and in this respect experiences a restriction. In a third method step S3, a 2D fluoroscopy image is recorded (with the C-arm for instance). In a further imaging method step S4, a 2D projection 14 is generated from the segmented 3D data set in a purely computational manner, said 2D projection image 14 being congruent with the current intraoperative 2D fluoroscopy image 15 according to the current C-arm position, in line with variables and spatial orientation.

This 2D projection is automatically generated from the segmented 3D data set by means of known 2D/3D registration methods according to the prior art, in an image-based or marker-based manner for instance.

In a fifth method step S5, the contours of the visible volume components of the 2D projection are determined with known segmentation methods and are optionally approximated by graphic primitives (lines, curve segments, splines etc.), so as to achieve a reduced 2D projection 16. This reduced 2D projection 16 is identical to the 2D fluoroscopy image in terms of its geometry, except that it contains the contour of the region 6 of interest as the only image information in this perspective.

In a sixth and tentative last method step S6, the reduced 2D projection 16 and thus the contour of the region 6 of interest is overlaid on the 2D fluoroscopy image 15.

This finally results in a cumulative image 17 on the monitor 10 of the image processing device according to FIG. 1, in which cumulative image the medical instrument 11 is displayed relative to the sharply delimited contour of the region of interest in the current C-arm position. The anatomy of the surrounding (background) tissue (the head 7 in FIG. 1 for instance) is only shown as a low-contrast image.

In a particularly advantageous embodiment of the method according to the invention, in a further seventh method step S7, a change in the angulation of the C-arm and/or further changes in system parameters or also patient movements are monitored (via the navigation system S for instance) and in an eighth method step S8 the overlayed graphic is deleted, if the displayed contour no longer applies. In this case, the method begins again with step S4, whereby a new reduced 2D projection corresponding to the new C-arm configuration is determined. The speed of the method is dependent on the computing power of the control and processing device 8, which is, as expected, so fast that the user may anticipate a contour overlay in real-time.

In summary, the inventive method provides the following advantages:

By segmenting the preoperative 3D raw data set, narrowly defined, anatomically sensible boundaries in the shape of sharp contours can be described.

These boundaries are considerably better visualized by overlaying these contours with the 2D fluoroscopy images (intraoperative and/or live recording images), than when a complete 3D raw data set is overlayed with the current fluoroscopy image. By displaying the contours with graphic primitives in accordance with the invention, the boundaries are sharper and more clearly delimited than is possible by methods available at present.

With intraoperative changes in the 2D fluoroscopy image (e.g. by moving the C-arm and/or changing system parameters such as zoom, SID, table movement or patient movement for instance), the contours can be automatically and continually updated so that an observer is given a spatial impression of the anatomical structure on the overplayed 2D fluoroscopy image during the parameter change. When a contrast medium is used, this method has the advantage that additional contrast medium need not be administered for a new angulation and on the other hand the contours are available immediately and without further interaction on the part of the user.

The invention claimed is:

1. A method for visualizing a contour of an interest region in a medical fluoroscopy image, comprising:
   firstly generating a 3D raw data set comprising the interest region with which the interest region is visible in a surrounding tissue by an imaging modality;
   secondly generating a segmented 3D data set from the 3D raw data set with which the interest region is delimited from the surrounding tissue by a processing device;
   thirdly generating a 2D fluoroscopy image which contains the interest region by an x-ray device;
   fourthly generating a 2D projection from the segmented 3D data set which is congruent with the 2D fluoroscopy image by the processing device;
   determining the contour of the interest region in the 2D projection by the processing device; and
   overlaying the contour with the 2D fluoroscopy image by the processing device.

2. The method as claimed in claim 1, wherein the 2D fluoroscopy image is intraoperatively obtained with the x-ray device.

3. The method as claimed in claim 2, wherein the x-ray device is a C-arm.

4. The method as claimed in claim 2, wherein the 2D fluoroscopy image is monitored for an interoperative change.

5. The method as claimed in claim 4, wherein the fourthly generating, determining, and overlaying steps are repeated for the interoperative change monitored in the 2D fluoroscopy image.

6. The method as claimed in claim 1, wherein the 3D raw data set is obtained preoperatively with the imaging modality.

7. The method as claimed in claim 1, wherein the interest region is delimited by an automatic or a manual segmentation.

8. The method as claimed in claim 1, wherein the 2D projection is generated by a 2D-3D registration.

9. The method as claimed in claim 8, wherein the 2D-3D registration is carried out in an image-based or a marker-based method.

10. The method as claimed in claim 1, wherein the contour is determined by an automatic or a manual segmentation.

11. The method as claimed in claim 1, wherein the contour is simulated by a graphic selected from the group consisting of: lines, curves, and splines.

12. The method as claimed in claim 1, wherein the interest region is an examination area of a human patient.

13. A device for visualizing a contour of an interest region in a medical fluoroscopy image, comprising:
    an x-ray device for recoding a 2D fluoroscopy image which contains the interest region;
    a storage unit for storing a 3D raw data set comprising the interest region with which the interest region is visible in a surrounding tissue; and
    a processing device that:
       generates a segmented 3D data set from the 3D raw data set with which the interest region is delimited from the surrounding tissue,
       creates a 2D projection from the segmented 3D data set which is congruent with the 2D fluoroscopy image,
       determines the contour of the interest region in the 2D projection, and
       overlays the contour with the 2D fluoroscopy image.

14. The device as claimed in claim 13, wherein the interest region is an examination area of a human patient.

15. The device as claimed in claim 13, wherein the x-ray device is a C-arm.

16. The device as claimed in claim 15, wherein the device comprises a navigation system which detects a position of the C-arm, a position of a medical instrument, and the patient.

* * * * *